US00PP16203P3

(12) United States Plant Patent
Zampini

(10) Patent No.: US PP16,203 P3
(45) Date of Patent: Jan. 17, 2006

(54) GOLDEN AND BURGUNDY VARIEGATED PIGMY BARBERRY PLANT NAMED 'GORUZAM'

(50) Latin Name: *Berberis thunbergii*
Varietal Denomination: Goruzam

(76) Inventor: James W. Zampini, c/o Lake County Nursery, Rte. 84, Box 122, Perry, OH (US) 44081-0122

( * ) Notice: Subject to any disclaimer, the term of this patent is extended or adjusted under 35 U.S.C. 154(b) by 130 days.

(21) Appl. No.: 10/866,821

(22) Filed: Jun. 15, 2004

(65) Prior Publication Data

US 2005/0278814 P1 Dec. 15, 2005

(51) Int. Cl.
*A01H 5/00* (2006.01)

(52) U.S. Cl. ..... Plt./241

(58) Field of Classification Search ..... Plt./241
See application file for complete search history.

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of *Berberis thunbergii* plant is provided that was the result of controlled breeding. A dwarf, generally compact, broad, and low-mounding growth habit is displayed. New foliage bears a bright red-purple coloration, and the mature foliage displays attractive variegation. The margins of the mature foliage are golden and the center is dark burgundy. A rapid growth rate between internodes of relatively short length is displayed. The plant is well suited for providing attractive ornamentation in the landscape.

7 Drawing Sheets

Botanical/commercial classification: *Berberis thunbergii*/ Pigmy Barberry Plant.
Varietal denomination: cv. 'Goruzam'.

SUMMARY OF THE INVENTION

The new Barberry plant of the present invention was created during 1978 by artificial pollination wherein two parents were crossed at 5052 South Ridge Road, Perry, Ohio, U.S.A., which previously had been studied in the hope that they would contribute the desired characteristics. The female parent (i.e., the seed parent) was *Berberis thunbergii* 'Atropurpurea Nana' (non-patented in the United States). The male parent (i.e., the pollen parent) was *Berberis thunbergii* 'Bogozam' (U.S. Plant Pat. No. 8,215). The parentage of the new variety can be summarized as follows:

'Atropurpurea Nana'×'Bogozam'

The seeds resulting from the above cross were sown and plants were obtained which were physically and biologically different from each other. Selective study resulted in the identification during 1980 of a single plant of the new variety. My attention was attracted to the plant of the present invention in view of its distinctive combination of characteristics that differs from each of its parents and from all other *Berberis thunbergii* varieties of which I am aware.

It was found that the new Barberry plant of the present invention exhibits the following combination of characteristics:

(a) exhibits a rapid growth rate between internodes of relatively short length, (b) exhibits a dwarf, generally compact, broad, and low-mounding growth habit, (c) forms new foliage having a bright red-purple coloration, and (d) forms attractive variegated mature leaves having golden margins and a dark burgundy center.

The new variety well meets the needs of the horticultural industry and can be grown to provide distinctive colorful ornamentation in the landscape. The bright red-purple new foliage displays a fluorescent appearance. No fruit has been formed during observations to date.

The new variety of the present invention can be readily distinguished from its parental varieties. More specifically, the 'Atropurpurea Nana' variety forms mature foliage that is consistently red-purple in coloration, and the 'Bogozam' variety forms mature leaves that are consistently yellow in coloration. Accordingly, neither parental variety displays the variegated mature foliage of the new variety. Also, the flowers of 'Atropurpurea Nana' parent are gold tinged with purple, and those of the 'Bogozam' parent are white and pink unlike the flowers of the new variety of the present invention that are pale yellow blushed on the outside with pinkish maroon. 'Atropurpurea Nana' additionally lacks a dwarf growth habit.

Other Barberry varieties such as 'Rosy Glow' (non-patented in the United States) and 'Griruzam' (non-patented in the United States) lack the dwarf growth habit of the new variety of the present invention. Also, the 'Rosy Glow' and 'Griruzam' varieties display flowers having colors that differ from that of the new variety of the present invention. More specifically, the 'Rosy Glow' variety forms gold colored flowers and the 'Griruzam' variety forms white flowers.

Plants of the new variety have been asexually reproduced at Perry, Ohio, U.S.A., through the use of softwood cuttings. The characteristics of the new variety have been found to be strictly transmissible by such asexual propagation, and the new variety reproduces true to type from one generation to another.

The new variety of the present invention has been named 'Goruzam'.

BRIEF DESCRIPTION OF THE PHOTOGRAPHS

The accompanying photographs show as nearly true as it is reasonably possible to make the same in color illustrations of this character, typical specimens of the new variety in various stages of development. The depicted specimens were being grown at Perry, Ohio, U.S.A.

Figure 1:
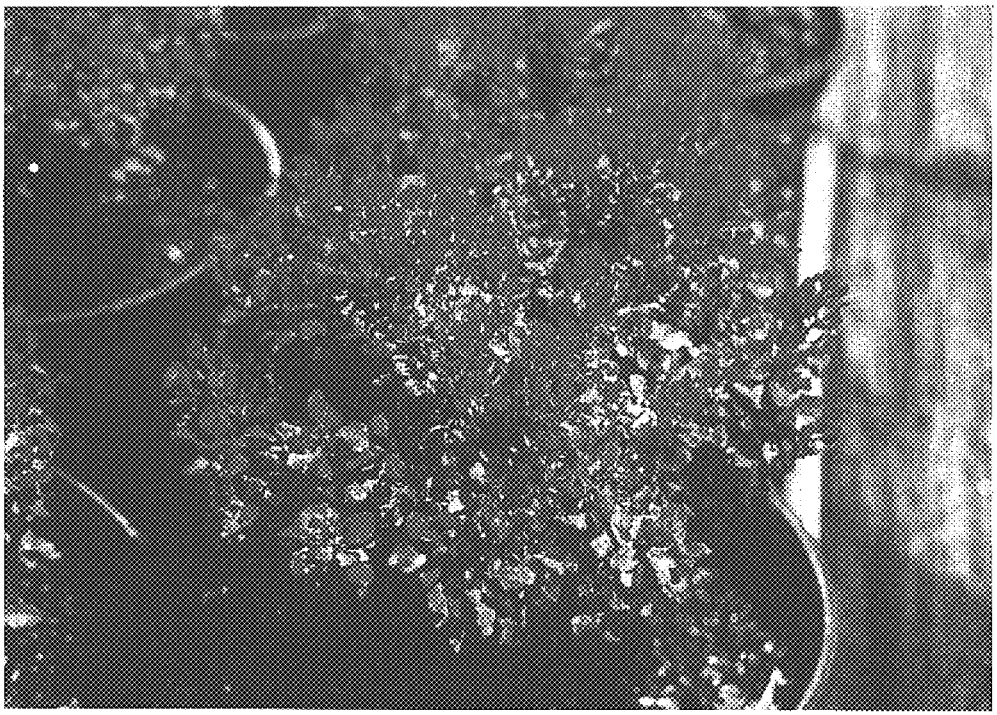
FIG. 1 illustrates a specimen of a six year-old plant of the new variety while being grown in a container during early spring. The bright fluorescent red-purple coloration of the newly-formed leaves is illustrated.
Figure 2:
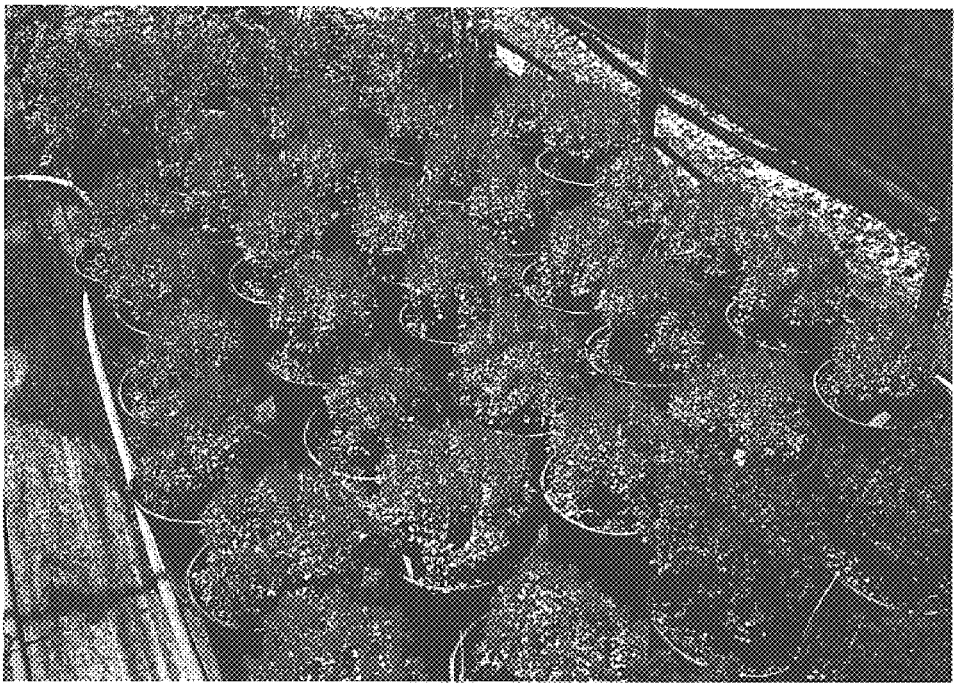
FIG. 2 illustrates at the center specimens of a large group of six year-old plants of the new variety during early spring wherein the bright fluorescent red-purple coloration of the newly-formed leaves further is illustrated. For comparative purposes at the lower right corner and in the background plants of previously known pygmy Barberry cultivars are included.
Figure 3:
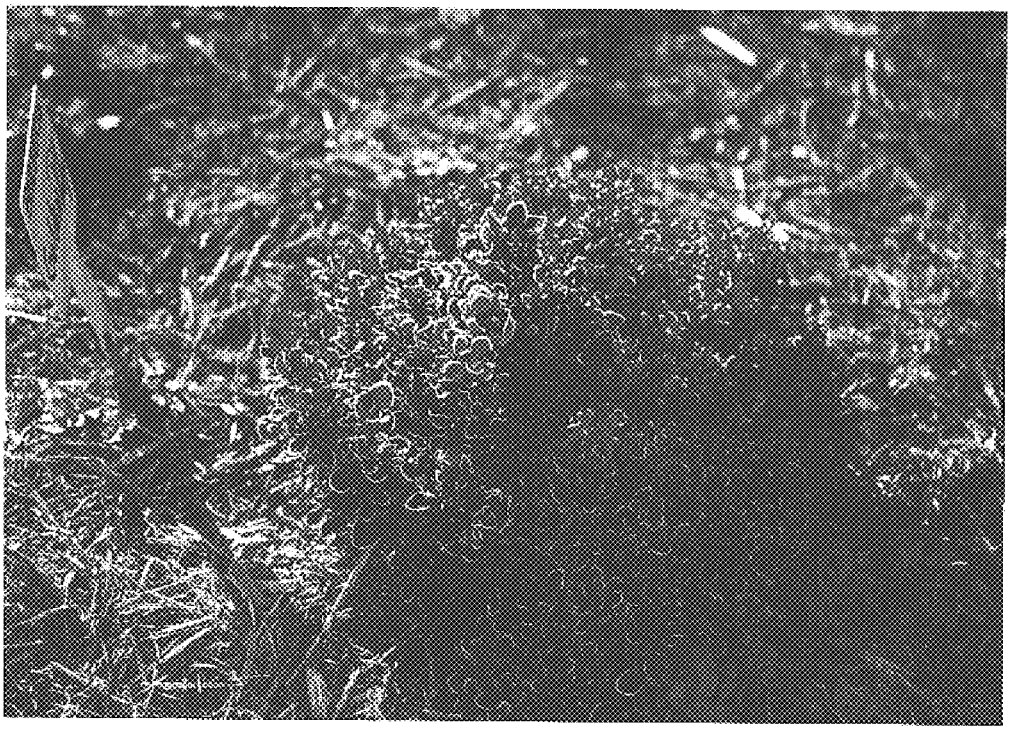
FIG. 3 illustrates later in the spring a plant of the new variety wherein the dwarf, generally compact, broad, low-mounding growth habit is illustrated as well as the beginning presence of golden coloration at the margins of the leaves.
Figure 4:
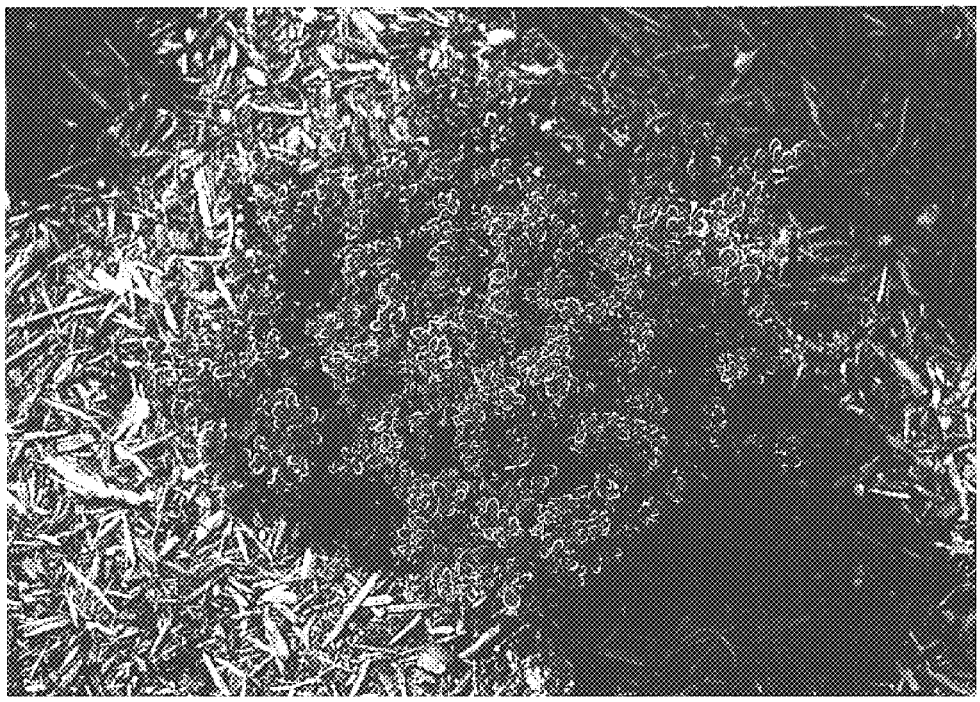
FIG. 4 illustrates during the summer a fifteen year-old plant of the new variety wherein the highly attractive mature variegated foliage displays golden edges and burgundy centers.
Figure 5:
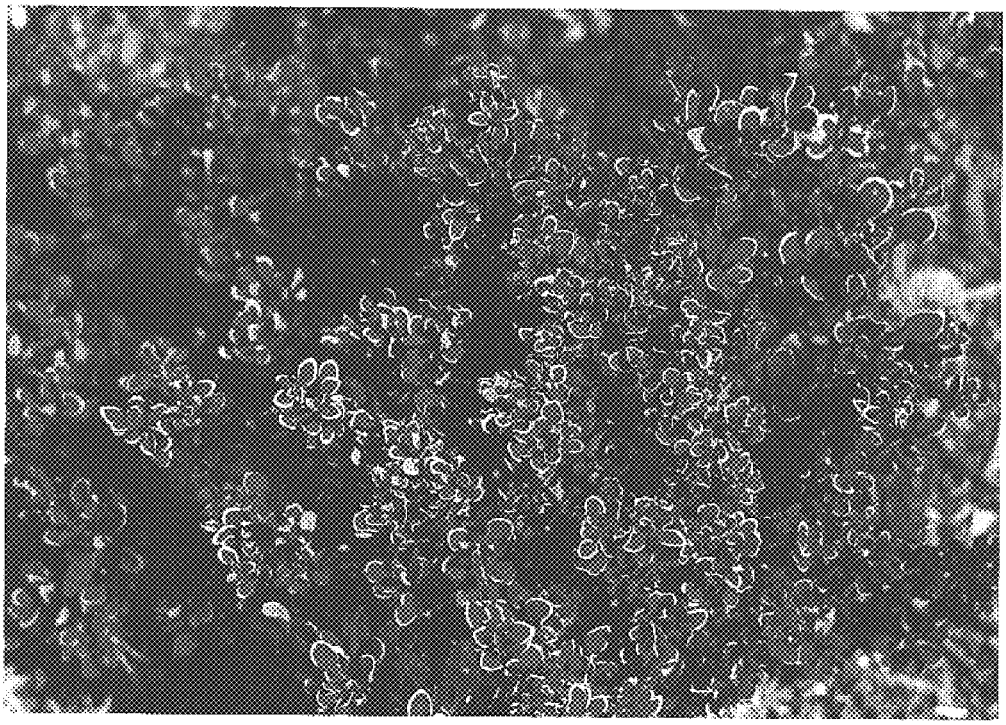
FIG. 5 illustrates a closer view of a portion of the fifteen year-old plant of FIG. 4 during the summer.
Figure 6:
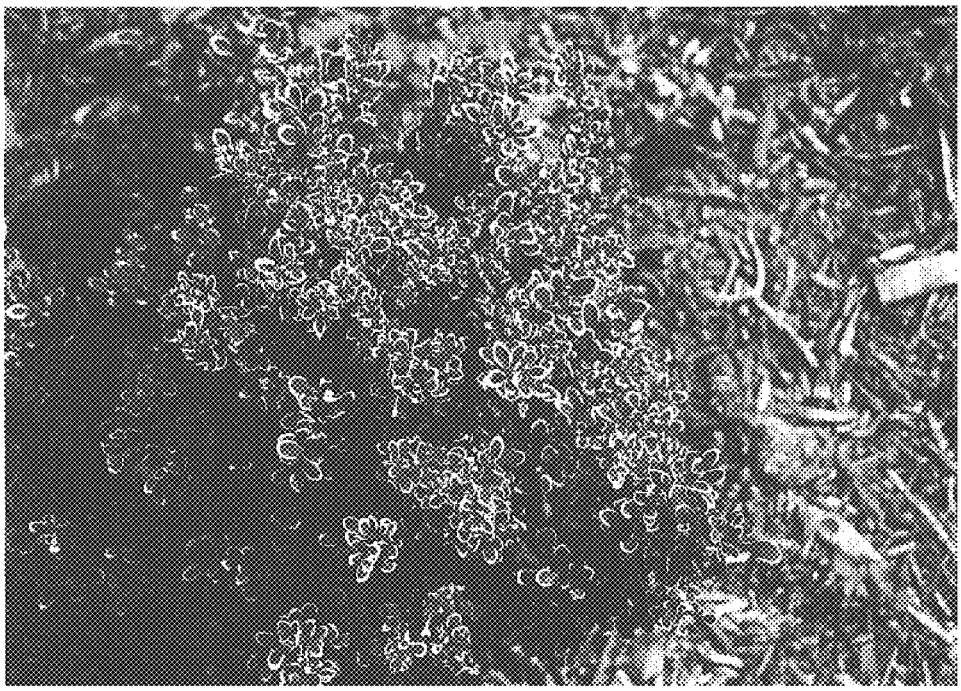

FIG. 6 illustrates the fifteen year-old plant of FIG. 4 during early fall at the end of the growing season. The golden margins of the leaves have become wider at this stage in their development. Such coloration is well retained throughout the fall.

Figure 7:
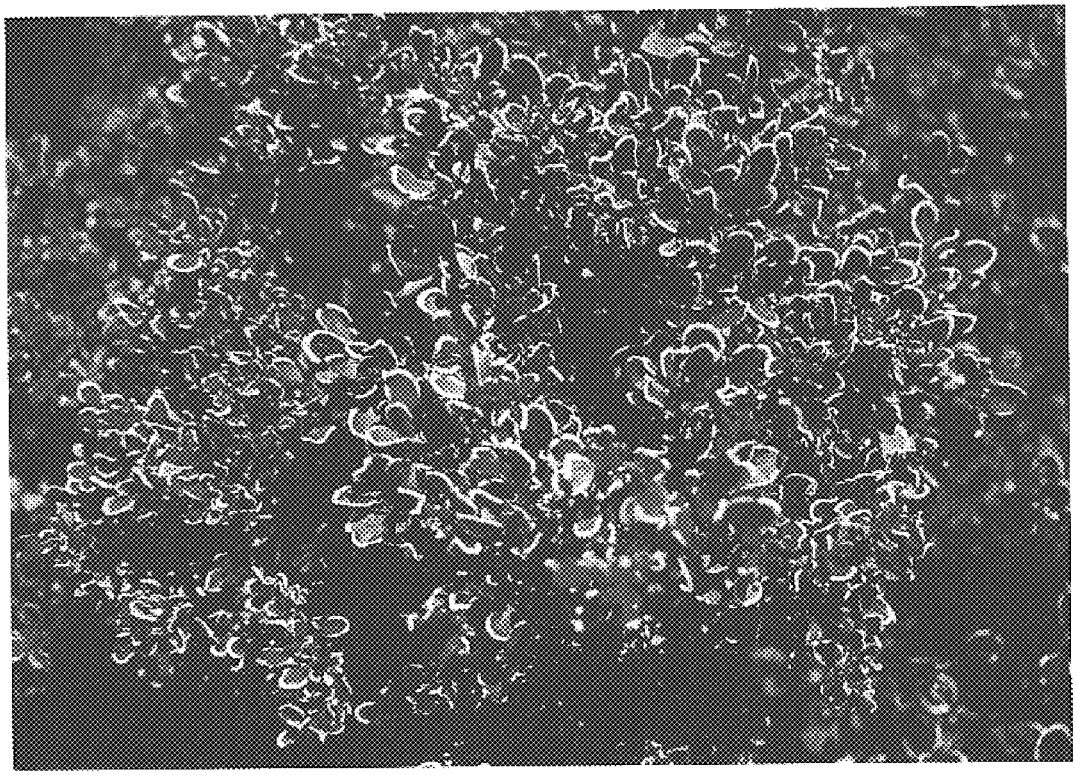

FIG. 7 illustrates a closer view of the fifteen year-old plant of FIG. 6 during early fall.

DETAILED DESCRIPTION

The chart used in the identification of color is The R.H.S. Colour Chart of The Royal Horticultural Society, London, England. Other reference to color is to be accorded its ordinary dictionary significance. The description is based upon the observation of plants of the new variety being grown at Perry, Ohio, U.S.A.

The original plant of the new variety exhibits a highly manageable dwarf (i.e., pygmy) growth habit and during 2004 is approximately 10 inches in height and approximately 16 inches in width. The growth habit also is generally compact, broad, and low-mounding. A rapid growth rate between internodes of relatively short length is displayed. The growth rate of the new variety exceeds that of its 'Atropurpurea Nana' parent. At full maturity based upon observations to date it is anticipated that the new variety of the present invention will assume a height of approximately 15 inches and a width of approximately 30 inches. Such dimensions are slightly less than those of the parent 'Bogozam' variety.

The vegetative parts of the new variety are typical of the genus except as specifically indicated hereafter. The entire, alternate, simple leaves are broadly elliptical with acuminate apices. The spine-tipped leaves are borne in clusters along the stems and are approximately ½ to 1 inch in length (including the petiole) narrowing at the base to the petiole which is commonly approximately ¼ to ½ inch in length.

The emerging leaves of the new variety in the spring are of a distinctive red-purple coloration. The leaves of the new variety in the spring on the upper surface commonly are near Red Group 45A and Red Group 46A with Red-Purple Group 59A, and on the under surface commonly are somewhat paler and are Red Group 47A and 47B with Green Group 143D and Yellow-Green Group 145D.

As the growing season progresses, a golden edge or margin forms on the leaves of the new variety and progressively widens. Also, the central portion of the leaves assumes a burgundy coloration. See FIGS. 3 to 7 in this regard. During mid-season, the golden margin is near Yellow Group 6B, and the burgundy center approximates Red Group 46B with Red-Purple Group 59B. During late summer, the golden edge widens and commonly is near Yellow Group 6A to Yellow Group 9A, and the burgundy center darkens somewhat to near Red Group 46A and Red Group 53A with Red-Purple Group 59A and Red-Purple Group 60A.

Immature twigs at the apex are near Red Group 45A and near Brown Group 200B at the base. Mature stems are lighter brown in coloration and approximate Brown Group 200D. The coloration of the leaf buds generally corresponds to that of the stems.

Pale yellow inconspicuous flowers are formed in sparse quantities in the springtime. The flower petal coloration is near Yellow Group 4D and commonly is blushed with pinkish-maroon on the outside that is near Red Group 51A and 51B. The fully open flowers are similar in size and configuration to those of the parental varieties and commonly measure approximately ¼ to ½ inch in diameter when fully open. The pedicel commonly measures approximately ½ inch. The reproductive parts of the new variety are substantially the same as those of the parental varieties and are typical of the genus.

During observations to date, no fruit has been found. Accordingly, the red ellipsoidal berries commonly formed by the parental varieties and the genus as a whole have not been formed by the new variety of the present invention.

No disease or insect problems have been noted during observations to date. Accordingly, the new variety appears to be disease resistant particularly with respect to rust, and appears to display good resistance to insects.

Plants of the new 'Goruzam' variety have not been observed under all possible environmental conditions to date. Accordingly, it is possible that the phenotypic expression may vary somewhat with changes in light intensity and duration, cultural practices, and other environmental conditions.

I claim:

1. A new and distinct Barberry plant having the following combination of characteristics:

(a) exhibits a rapid growth rate between internodes of relatively short length, (b) exhibits a dwarf, generally compact, broad, and low-mounding growth habit, (c) forms new foliage having a bright red-purple coloration, and (d) forms attractive variegated mature leaves having golden margins and a dark burgundy center;

substantially as illustrated and described.

* * * * *